United States Patent [19]

Hall et al.

[11] 4,082,627

[45] Apr. 4, 1978

[54] ELECTROLYTIC REDUCTION OF DIHYDROBENZOPYRANOXANTHENONES

[75] Inventors: David A. Hall, Indianapolis; Richard E. Heiney, Greenwood, both of Ind.

[73] Assignee: Eli Lilly and Company, Indianapolis, Ind.

[21] Appl. No.: 800,674

[22] Filed: May 26, 1977

[51] Int. Cl.$^2$ ............................................... C25B 3/04
[52] U.S. Cl. ................................. 204/59 R; 204/73 R
[58] Field of Search ........................... 204/59 R, 73 R

[56] References Cited

U.S. PATENT DOCUMENTS

| 3,361,653 | 1/1968 | Miller | 204/59 R |
|---|---|---|---|
| 3,444,059 | 5/1969 | Throop | 204/72 |
| 3,925,173 | 12/1975 | Junghans | 204/73 R |

FOREIGN PATENT DOCUMENTS

| 2,408,522 | 9/1975 | Germany | 204/73 R |

*Primary Examiner*—F.C. Edmundson
*Attorney, Agent, or Firm*—William C. Martens, Jr.; Arthur R. Whale

[57] ABSTRACT

Dihydrobenzopyranoxanthenones of the formula

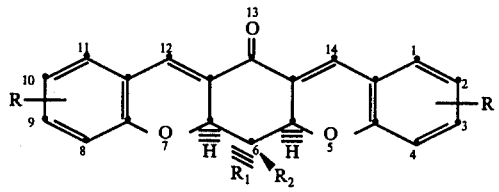

are electrolytically reduced to their corresponding hexahydrobenzopyranoxanthenones at a mercury cathode in the presence of a proton source and in the presence of an electrolyte selected from the group consisting of alkali metal salts, quaternary ammonium salts having a total of about 10 to about 28 carbon atoms in the cation moiety, and tertiary amine salts having a total of about 7 to about 21 carbon atoms in the cation moiety.

14 Claims, No Drawings

ELECTROLYTIC REDUCTION OF DIHYDROBENZOPYRANOXANTHENONES

BACKGROUND OF THE INVENTION

This invention relates to a process for preparing compounds having anti-androgen activity. Androgens are substances which are active in stimulating secondary sex characteristics in males. Although such substances obviously are of great physiological significance, they can produce certain undesirable side effects, and it would be highly advantageous to prophylactically or therapeutically eliminate or minimize these effects. For example, the stimulatory effects of androgens upon the prostate gland have been known for many years. The pathogenesis of benign prostatic hypertrophy (BPH) and/or prostatic cancer (PC) is not fully understood; however, it is thought that both of these syndromes are subject to the influence of androgens. In addition, acne, an inflammatory disease involving the sebaceous glands and found chiefly in adolescents, is thought to be dependent upon sebum secretion which, in turn, is dependent upon androgen action.

Androgens are steroidal hormonal agents. For some time, it has been customary to attempt control of androgen activity by administration of other steroids. However, although administration of these steroids may be effective in diminishing androgen action, their administration, in general, results in other unwanted side effects which limit their usefulness.

Recently, a class of compounds has been discovered which are non-steroidal in structure and which exhibit potent anti-androgen activity. These compounds are dihydrobenzopyranoxanthenones and hexahydrobenzopyranoxanthenones. In general, the latter are prepared by hydrogenation of the former. One of the methods for effecting this reduction constitutes the process of this invention. The process of this invention involves the electrolytic reduction of a dihydrobenzopyranoxanthenone to its corresponding hexahydrobenzopyranoxanthenone. The method of this invention, by appropriate selection of reaction conditions, provides unique direction and control of the stereoconfiguration of the hexahydro product which is formed.

SUMMARY OF THE INVENTION

As mentioned above, this invention relates to a process for electrolytically reducing a dihydrobenzopyranoxanthenone to its corresponding hexahydrobenzopyranoxanthenone.

Essentially, therefore, this invention is directed to a process for preparing a compound of the formula

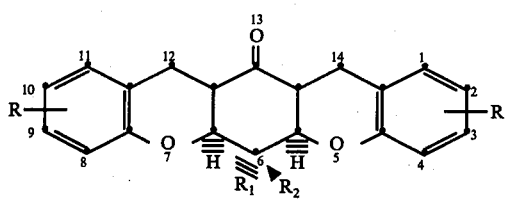

which comprises electrolytically reducing a compound of the formula

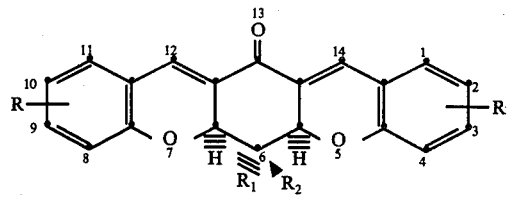

in which, in any of the above, each R is hydrogen, $C_1$-$C_4$ alkyl, $C_1$-$C_4$ alkoxy, hydroxy, cyano, or halo, and both R groups are identical and are symmetrically located; $R_1$ is $C_1$-$C_3$ alkyl and $R_2$ is methyl, or $R_1$ and $R_2$ taken together are —$CH_2$)$_n$ in which $n$ is an integer from 4 to 6; such electrolytic reduction being carried out at a temperature of from about 5° C. to about 80° C. in an organic or an aqueousorganic medium at a mercury cathode in the presence of a proton source and in the presence of an electrolyte selected from the group consisting of alkali metal salts, quaternary ammonium salts having a total of about 10 to about 28 carbon atoms in the cation moiety, and tertiary amine salts having a total of about 7 to about 21 carbon atoms in the cation moiety.

DETAILED DESCRIPTION OF THE INVENTION

The compounds produced by the process of this invention are classified generally as hexahydrobenzopyranoxanthenones and are produced from their corresponding dihydrobenzopyranoxanthenones.

In both the starting materials and the products of the process of this invention, the carbon in the 6-position completes a $C_5$-$C_7$ spiro ring or is substituted both with a methyl ($R_2$) and with the group $R_1$ in which $R_1$ is $C_1$-$C_3$ alkyl. As used herein, the term "$C_1$-$C_3$ alkyl" refers to methyl, ethyl, n-propyl, or isopropyl. When $R_1$ is methyl, a 6,6-dimethyl compound of course is defined. However, when $R_1$ is $C_1$-$C_3$ alkyl and is other than methyl, the substituents at the carbon in the 6-position are dissimilar, and, therefore, more than one isomer is possible. In those cases, the compounds involved in the process of this invention are those in which the methyl group ($R_2$) is in a position generally axial to the ring while the group $R_1$ is in a position generally equatorial to the ring.

Furthermore, in both the starting materials and the products of the process of this invention, the group R represents hydrogen, $C_1$-$C_4$ alkyl, $C_1$-$C_4$ alkoxy, hydroxy, cyano, or halo. As used herein, the term "$C_1$-$C_4$ alkyl" refers to methyl, ethyl, n-propyl, isopropyl, n-butyl, isobutyl, sec-butyl, and t-butyl. The term "$C_1$-$C_4$ alkoxy" as used herein refers to methoxy, ethoxy, n-propoxy, isopropoxy, n-butoxy, isobutoxy, sec-butoxy, and t-butoxy. As used herein, the term "halo" refers to chloro, fluoro, and bromo.

Furthermore, in both the starting materials and the products of the process of this invention, the group R appears at two points. In any particular compound, the group R at both points in the molecule represents the same moiety. Furthermore, the groups designated as R, in any particular compound of the process of this invention, are located symmetrically, and, thus, are at the 2- and 10-positions, the 3- and 9-positions, or the 4- and 8-positions.

In the dihydrobenzopyranoxanthenone starting materials of the process of this invention, a hydrogen atom appears in both the 5a- and the 6a-positions. In accordance with this invention, it is essential that the stereoconfiguration of these hydrogen atoms be such that both are located on the same side relative to the major plane of the molecule. In other words, both hydrogens must be in the α-position, or, what is equivalent, in the β position.

The dihydrobenzopyranoxanthenones in which the 5a- and 6a-hydrogens are on opposite sides of the major plane of the molecule, that is, those in which the 5a-hydrogen is in the α-position and the 6a-hydrogen is in the β-position, or vice versa, are useful as intermediates in the preparation of the starting materials of the process of this invention. They are readily epimerized to the starting material dihydrobenzopyranoxanthenones by simply warming the compound to a temperature moderately above room temperature.

The hexahydrobenzopyranoxanthenones produced by the process of this invention differ from the dihydro compounds by hydrogenation of the double bonds at the 12- and 13a-carbons. The resulting hydrogenated products contain hydrogens at the 5a, 6a, 12, 12a, 13a, and 14-carbons. The particular stereoconfiguration of the hydrogens at the 5a, 6a, 12a, and 13a-carbons, relative to each other is a principal factor in the process of this invention. Of the various stereochemical combinations which are possible from these four hydrogens, two combinations are dominating and important products available from this invention. The following two moieties of the hexahydrobenzopyranoxanthenones represent the principal products available from the process of this invention.

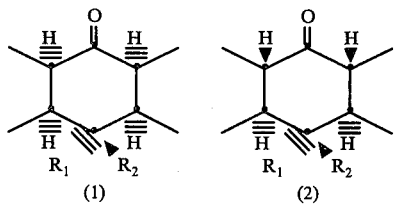

From the above, it is apparent that the principal hexahydrobenzopyranoxanthenones prepared by the process of this invention comprise those in which (1) the hydrogens at the 5a- and the 6a-carbons are cis each to the other and (2) the hydrogens at the 12a- and the 13a-carbons are cis each to the other.

In addition to the above limitations pertaining to the stereoconfiguration of the compounds produced by the process of this invention, a further limitation exists. The group $R_1$ can be a $C_1$–$C_3$ alkyl group. In those instances in which $R_1$ is methyl, a 6,6-dimethyl compound is defined, and no further stereoconfiguration considerations arise. However, when $R_1$ is other than methyl, a 6-methyl-6-ethyl, a 6-methyl-6-n-propyl, or a 6-methyl-6-isopropyl compound is defined. All of these represent compounds available from the process of this invention; however, the stereoconfigurational aspects are such that the compounds are restricted to those in which $R_1$ is in a position equatorial to the ring structure, and the methyl group ($R_2$) is in a position axial to the ring structure. In other words, the compounds involved in the process of this invention in which $R_1$ is $C_1$–$C_3$ alkyl and is other than methyl, both starting materials and products, are those in which the 5a and 6a hydrogens and the $R_1$ group are all in the α-position.

The dihydrobenzopyranoxanthenone starting materials of the process of this invention are prepared by condensation of a 2-hydroxybenzaldehyde with a 4-methyl-4-alkyl-2,5-cyclohexadienone in the presence of pyrrolidine and acetic acid. This reaction is depicted as follows:

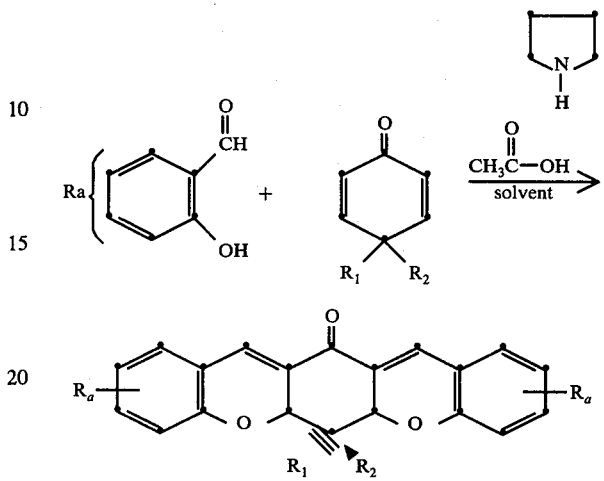

In the foregoing reaction, $R_a$ is hydrogen, $C_1$–$C_4$ alkyl, $C_1$–$C_4$ alkoxy, cyano, or halo. The reaction is carried out at a temperature of from about 0° C. to about 65° C. When the reaction is carried out at about room temperature or below and $R_1$ is methyl, the product which results in a mixture of the 5aα, 6aβ- and the 5aβ, 6aα-optical isomers. This product, upon being subjected to a temperature above room temperature, rearranges to the 5aα, 6aα-isomer, the starting material of the process of this invention and itself a potent anti-androgen.

When the condensation of the 2-hydroxybenzaldehyde with a 4-substituted-2,5-cyclohexadienone is carried out at a temperature above room temperature, and generally from about 55° C. to about 65° C., the 5aα, 6aα-isomer product is isolated directly from the reaction mixture.

As is evident from the products obtained from the above reaction, at least a 2:1 molar ratio of the 2-hydroxybenzaldehyde to the 4-substituted-2,5-cyclohexadienone is required.

The condensation customarily can be carried out in any solvent which is inert to the reactants and which affords sufficient solubility for the reactants. In the event that epimerization affording direct isolation of the 5aα, 6aα-isomer is desired, the boiling point of the solvent must be high enough to achieve this result, that is, the boiling point must be in excess of about room temperature. Typical solvents which are employed include aromatic hydrocarbons, such as benzene, toluene, and the like, and ethers such as tetrahydrofuran, and the like. A proton source is employed, generally in an amount at least equivalent on a molar basis to the amount of the aldehyde which is employed. Typical proton sources include carboxylic acids such as acetic acid, propionic acid, butyric acid, and the like. The preferred acid is acetic acid. In addition, a secondary amine is employed, generally in an amount at least equivalent on a molar basis to the amount of carboxylic acid which is employed, and preferably in approximately a 10% molar excess relative to the carboxylic acid. Typical such secondary amines include, for example, pyrrolidine, piperidine, morpholine, and the like. The preferred secondary amine is pyrrolidine.

In carrying out the condensation, the reactants are mixed in the solvent of choice. The order of addition of the reactants is not critical; normally, however, the cyclohexadienone is added last. The mixture then is permitted to react at the selected temperature of reaction, and the product is recovered by customary techniques.

The starting materials employed in the condensation used to produce the dihydrobenzopyranoxanthenone starting materials of this invention are salicylaldehyde or a substituted salicylaldehyde and a 4-substituted-2,5-cyclohexadienone.

Salicylaldehyde as well as the 3-, 4-, or 5-substituted salicylaldehydes are available by techniques well recognized in the art. They, for example, can be prepared by the Reimer-Tiemann reaction which involves treatment of the appropriately substituted phenol with chloroform and an alkali metal hydroxide, particularly sodium hydroxide.

The dienone is available by either of two relatively complex reaction sequences which can be depicted as follows:

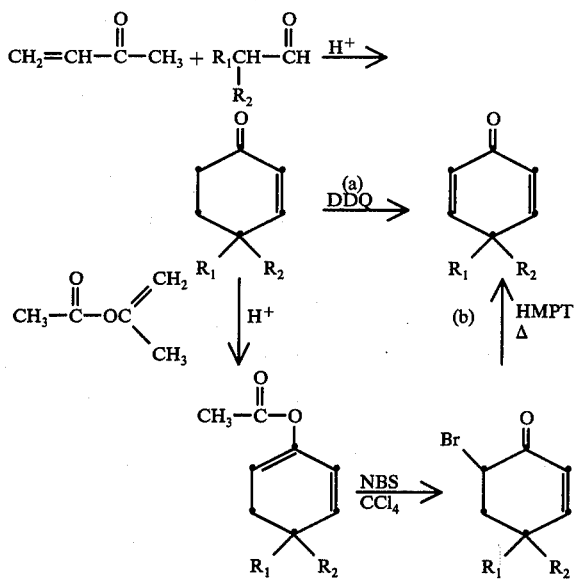

The formation of 4-substituted-cyclohexenones from methyl vinyl ketone and the appropriate aldehyde is well known from E. L. Eliel and C. Lukach, *J. Am. Chem. Soc.*, 79, 5986 (1957) and from Y. Chan and W. W. Epstein, *Org. Syn.*, 53, 48 (1973). It further has been discovered that this method is improved when carried out under acidic instead of alkaline conditions and in a manner analogous to that described for cyclic ketones by C. H. Heathcock et al., *Tetrahedron Letters*, 4995 (1971).

The condensation of methyl vinyl ketone with the aldehyde is readily controlled and may be carried out neat or in the presence of an inert solvent suitable for azeotropic removal of the water formed as by-product. An equimolar quantity of methyl vinyl ketone and the aldehyde or a moderate excess of up to about 10 percent of the aldehyde generally is employed. As indicated, the condensation preferably is carried out under acidic conditions. Although any of several strong acids can be used, sulfuric acid, methanesulfonic acid, benzenesulfonic acid, p-toluenesulfonic acid, and such like acids, are preferred. The condensation is exothermic, and, therefore, care must be exercised during the initial exothermic phase to avoid excessive temperature rise such as would cause polymerization of the methyl vinyl ketone.

Conversion of the 4-substituted-cyclohexenone to the desired product can be accomplished by either of two routes. The direct conversion (Route a) involves a dehydrogenation using dichlorodicyanoquinone (DDQ) in accordance with the literature procedure of H. E. Zimmerman et al., *J. Am. Chem. Soc.*, 93, 3653 (1971). Alternatively, the conversion can be achieved indirectly (Route b) by the sequence described in H. Plieninger et al., *Chem. Ber.*, 94, 2115 (1961). This sequence involves treating the 4-substituted-cyclohexenone with propen-2-yl acetate under acidic conditions to produce a 2-acetoxy-5-substituted-1,3-cyclohexadiene. The latter is treated with N-bromosuccinimide to produce a 4-substituted-6-bromocyclohex-2-enone which then is dehydrobrominated to the desired cyclohexadienone using hexamethylphosphoric triamide (HMPT). The use of HMPT is documented in Fieser and Fieser, *Reagents for Organic Synthesis*, Volume II, John Wiley and Sons, Inc., New York, 1969, pp. 209–210.

The starting materials of the process of this invention in which the group R is hydroxy are prepared by The dihydrobenzopyranoxanthenone is dissolved or suspended in an organic medium or in a medium comprising an aqueous-organic mixture. The aqueous-organic mixture itself can present as an emulsion or as a miscible combination. Typical useful organic media include amides, such as N,N-dimethylformamide, N,N-dimethylacetamide, and the like; nitriles, such as acetonitrile, demethylation of the corresponding compounds in which R is methoxy. Demethylation is accomplished by treating the dimethoxy compound with boron tribromide. Typically, three molar equivalents of boron tribromide are added to a mixture of the dimethoxy compound in an inert solvent. The addition is accomplished as rapidly as possible while retaining the temperature of the reaction mixture at about 0° C. Upon completion of the addition, the mixture is allowed to warm to room temperature and is maintained at room temperature for about 4 to about 16 hours. Product recovery is accomplished by adding the mixture to ice water and extracting the product into an appropriate solvent, such as, for example, methylene chloride, ethyl acetate, and the like.

The hexahydrobenzopyranoxanthenones are prepared in accordance with the process of this invention by electrolytic reduction of the corresponding dihydrobenzopyranoxanthenones. Accordingly, a dihydrobenzopyranoxanthenone is reduced at the cathode of an electrolytic cell to provide, via a four electron reduction, the corresponding hexahydrobenzopyranoxanthenone. This process is illustrated by the following general reaction scheme.

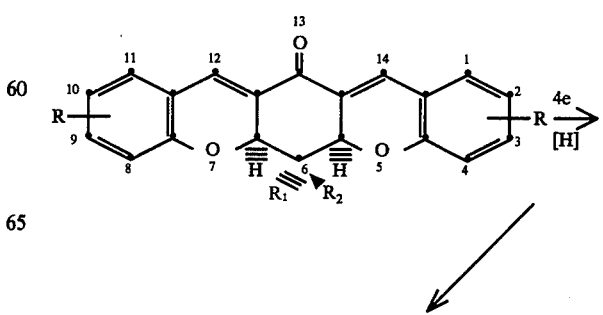

-continued

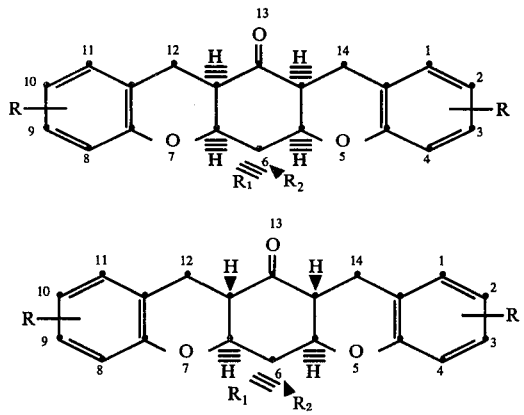

The dihydrobenzopyranoxanthenone is dissolved or suspended in an organic medium or in a medium comprising an aqueous-organic mixture. The aqueous-organic mixture itself can be present as an emulsion or as a miscible combination. Typical useful organic media include amides, such as N,N-dimethylformamide, N,N-dimethylacetamide, and the like; nitriles, such as acetonitrile, and the like; alcohols, such as methanol, ethanol, and the like; aromatic hydrocarbons, such as benzene, toluene, and the like; halogenated hydrocarbons, such as methylene chloride, chloroform, and the like; and such other organic media. Organic media which are preferred for use in the electrolysis process of this invention are amides, nitriles, and alcohols. Specifically preferred media include N,N-dimethylformamide, acetonitrile, and methanol. An especially preferred organic medium is methanol.

In addition, an electrolyte is added to the mixture. Useful electrolytes are salts such as halides, tosylates, perchlorates, and the like, of the alkali metals, such as lithium, sodium, and potassium. Other useful electrolytes are quaternary ammonium salts, such as halides, perchlorates, and the like. These include tetraalkylammonium, trialkylaralkylammonium, dialkyldiaralkylammonium, or alkyltriaralkylammonium, any of which have a total of about 10 to about 28 carbon atoms in the cation moiety. A preferred such salt is the tetrabutylammonium salt. A further class of electrolytes are tertiary amine salts, and these include halides, tosylates, perchlorates, and the like, of trialkylamines, dialkylaralkylamines, alkyldiaralkylamines, and triaralkylamines, any of which have a total of from about 7 to about 21 carbon atoms in the cation moiety. A preferred tertiary amine salt is a salt of tributylamine, and in particular, p-toluenesulfonic acid salt.

Examples of typical electrolytes include lithium perchlorate, potassium perchlorate, sodium perchlorate, lithium chloride, potassium bromide, sodium fluoride, sodium iodide, lithium iodide, tricaprylylmethylammonium chloride, benzyltributylammonium chloride, benzyltriethylammonium bromide, benzyltriethylammonium chloride, benzyltrimethylammonium bromide, cetyltrimethylammonium bromide, methyltributylammonium iodide, myristyltrimethylammonium bromide, tetrabutylammonium bromide, tetrabutylammonium chloride, tetrabutylammonium iodide, dibenzyldiethylammonium chloride, dibenzyldipropylammonium bromide, phenethyltributylammonium chloride, diphenethyldipentylammonium bromide, tribenzylethylammonium chloride, tetrahexylammonium chloride, triheptylbenzylammonium bromide, tripropylphenethylammonium iodide, tributylphenethylammonium chloride, N,N-diisopropyl-N-ethylamine perchlorate, tri-n-hexylamine bromide, N-benzyl-N,N-diethylamine p-toluenesulfonate, N-benzyl-N,N-dibutylamine bromide, N,N-dibenzyl-N-butylamine perchlorate, N,N-dibenzyl-N-ethylamine chloride, tribenzylamine p-toluenesulfonate, tributylamine chloride, and the like.

Furthermore, a source of protons is included in the reaction medium. This is found to expedite the electrolytic reduction defined by the process of this invention. Relatively weak acids having $pK_a$ values of from about 2 to about 6, such as benzoic acid, acetic acid, and the like, produce best results. Weaker acids, such as water, phenol, and the like, provide relatively poorer results, perhaps due to insufficient hydrogen ion activity. Strong acids, such as sulfuric acid, produced a hydrogen discharge at a potential lower than that required to effect the desired reduction, thereby preventing formation of the desired product.

As previously indicated, the dihydrobenzopyranoxanthenone substrate is reduced in an appropriate organic medium and in the presence of a selected electrolyte. In general, the substrate is present in an amount of from about 1 to about 15 mg. per ml. of medium. The electrolyte, in general, is present in an amount of from about 0.01 M to about 1.0 M, and, generally, the acid is present in an amount of about 1–5% by weight based upon the volume of the medium. The electrolytic reduction, in general, is carried out at a temperature of from about 5° C. to about 80° C., and, conveniently at about 20° C. to about 30° C.

The resulting mixture, containing the dihydrobenzopyranoxanthenone substrate, proton source, electrolyte, and organic or organic-aqueous medium, is placed in contact with the cathode of an electrolytic cell. A potential corresponding to a point at the foot of background discharge is applied. The potential is determined by preparing a current vs. potential curve at the working electrode on the medium prior to electrolysis. Current at the determined potential then is allowed to pass through the cell until an amount of current corresponding to between one and two times the number of Faradays required for a four-electron reduction has passed. The electrolytic process of this invention is an especially convenient cathode reduction process which occurs with ease in commonly constructed electrolysis apparatus. For example, the present process can be carried out using a conventional electrolytic cell, such as any of those described by M. J. Allen, *Organic Electrode Processes,* Reinhold Publishing Corporation, New York, 1958. These conventional electrolytic cells are described at page 33 of the publication and comprise a suitable cathode and anode separated by a bridge. The cathode which is used in the process of this invention is mercury. Anodic materials which can be used include platinum and carbon. Platinum metal is a preferred anode and particularly when it is in the form of a fine gauze or a wire mesh. Carbon, due to its low cost, represents another preferred anode.

The bridge connecting the cathode and anode can be a conventional salt bridge such as, for example, a 4 percent aqueous mixture saturated with potassium chloride. It can also be a suitable porous membrane such as, for example, an ion-exchange membrane, a ceramic membrane, or a sintered glass membrane of small to medium porosity. Any of those membranes described and discussed by N. J. Allen, supra, can as well be employed.

A typical electrolytic cell in which the process of this invention is carried out comprises a jacketed glass cylindrical cathode compartment in which a glass anode compartment, part of which is a glass frit, is suspended. In general, the cathode is present as a ring-shaped pool of mercury. The anode compartment generally is a fritted glass cylinder or a circular double-walled glass tube having a circular glass frit sealed into its lower end. In general, the anode comprises a platinum wire immersed in the same mixture of the organic or organic-aqueous medium and electrolyte as is used in the cathode compartment. Normally, the electrolysis cell is stoppered with a cap through which a deaerating frit, a reference probe, and a thermometer are inserted. The reference electrode probe comprises a glass tube containing a fiber-junction in which a saturated calomel electrode is inserted.

In practice, the appropriate mixture containing the organic or organic-aqueous medium, electrolyte, and proton donor, is placed into the cathode compartment. A predetermined quantity (about 1–15 mg./ml.) of the dihydrobenzopyranoxanthenone is added to the stirred mixture, and the circular anode compartment containing the mixture of organic or organic-aqueous medium and electrolyte together with the electrolysis cell cap is properly positioned relative to the cathode. Argon then is introduced through the deaerating frit and into the stirred cathode mixture. Upon completion of deaeration (about 15 minutes), the deaerating frit is raised to a position above the surface of the cathode solution, and the flow of argon is continued throughout the electrolysis. A predetermined potential then is applied to the cell until an amount of current has passed which corresponds to approximately twice the number of Faradays required for a four electron reduction. Calculation of the coulombs which have passed through the system can be determined by means of coulometer, and the system can also be monitored by means of thin-layer chromatography or high pressure liquid chromatography. Any of these methods are useful in determining the extent of reaction. Upon completion of the electrolysis, the catholyte solution is collected.

Workup of the reaction mixture is accomplished by routine techniques. In general, the majority of the organic or aqueous-organic medium first is removed in vacuo. The resulting syrupy residue then is dissolved in ethyl acetate. The ethyl acetate solution is washed several times with generally equal volume amounts of water to remove electrolyte as well as any proton donor which may have been employed. The ethyl acetate phase then is dried over a suitable drying agent, such as anhydrous magnesium sulfate, and is filtered. The ethyl acetate solvent is removed, and the residue is dried for several hours in a vacuum oven at about 45° C. The desired hexahydrobenzopyranoxanthenone product then is obtained by crystallization of the residue from an appropriate solvent system.

The structure of the cation of the electrolyte is an important factor in the process of this invention. It has been discovered that the stereoconfiguration of the hexahydrobenzopyranoxanthenone which is formed is to a great degree dependent upon the particular electrolyte which is used. When the electrolyte is a salt having a cation which forms a strongly associated ion pair, such as a lithium, sodium, or potassium cation, a product comprising predominantly the hexahydrobenzopyranoxanthenone having a 5a$\alpha$, 6a$\alpha$, 12a$\beta$, 13a$\beta$ configuration results. Conversely, an electrolyte having a cation which forms a weak ion pair, such as a quaternary ammonium salt or a tertiary amine salt, directs the electrolytic reduction to a product comprising predominantly the hexahydrobenzopyranoxanthenone having a 5a$\alpha$, 6a$\alpha$, 12a$\alpha$, 13a$\alpha$ configuration. Since, in general, the $\alpha,\alpha,\alpha,\alpha$-isomer is more active as an anti-androgen than is its $\alpha,\alpha,\beta,\beta$-isomer counterpart, it is highly preferred to employ a quaternary ammonium salt or a tertiary amine salt as electrolyte.

Examples of dihydrobenzopyranoxanthenone starting materials of the process of this invention are 6,6a$\alpha$-dihydro-6,6-dimethyl-5a$\alpha$H,13H-(1)benzopyrano(3,2-b)xanthen-13-one;

6,6a$\alpha$-dihydro-6$\beta$-methyl-6$\alpha$-ethyl-5a$\alpha$H,13H-(1)-benzopyrano(3,2-b)xanthen-13-one;

6,6a$\alpha$-dihydro-6$\beta$-methyl-6$\alpha$-n-propyl-5a$\alpha$H,13H-(1)benzopyrano(3,2-b)xantehn-13-one;

6,6a$\alpha$-dihydro-6$\beta$-methyl-6$\alpha$-isopropyl-5a$\alpha$H,13H-(1)benzopyrano(3,2-b)xanthen-13-one;

6,6a$\alpha$-dihydro-4,8-dimethyl-6,6-dimethyl-5a$\alpha$H,13H-(1)benzopyrano(3,2-b)xanthen-13-one;

6,6a$\alpha$-dihydro-3,9-diethyl-6,6-dimethyl-5a$\alpha$H,13H-(1)benzopyrano(3,2-b)xanthen-13-one;

6,6a$\alpha$-dihydro-2,10-di-n-propyl-6,6-dimethyl-5a$\alpha$H,13H-(1)benzopyrano(3,2-b)xanthen-13-one;

6,6a$\alpha$-dihydro-2,10-di-t-butyl-6$\beta$-methyl-6$\alpha$-ethyl-5a$\alpha$H,13H-(1)benzopyrano(3,2-b)xanthen-13-one;

6,6a$\alpha$-dihydro-3,9-dimethoxy-6,6-dimethyl-5a$\alpha$H,13H-(1)benzopyrano(3,2-b)xanthen-13-one;

6,6a$\alpha$-dihydro-4,8-diethoxy-6$\beta$-methyl-6$\alpha$-isopropyl-5a$\alpha$H,13H-(1)benzopyrano(3,2-b)xanthen-13-one;

6,6a$\alpha$-dihydro-4,8-diisopropoxy-6,6-dimethyl-5a$\alpha$H,13H-(1)benzopyrano(3,2-b)xanthen-13-one;

6,6a$\alpha$-dihydro-3,9-di-n-butoxy-6$\beta$-methyl-6$\alpha$-n-propyl-5a$\alpha$H,13H-(1)benzopyrano(3,2-b)xanthen-13-one;

6,6a$\alpha$-dihydro-4,8-dihydroxy-6,6-dimethyl-5a$\alpha$H,13H-(1)benzopyrano(3,2-b)xanthen-13-one;

6,6a$\alpha$-dihydro-3,9-dicyano-6$\beta$-methyl-6$\alpha$-ethyl-5a$\alpha$H,13H-(1)benzopyrano(3,2-b)xanthen-13-one;

6,6a$\alpha$-dihydro-4,8-dichloro-6$\beta$-methyl-6$\alpha$-isopropyl-5a$\alpha$H,13H-(1)benzopyrano(3,2-b)xanthen-13-one;

6,6a$\alpha$-dihydro-4,8-difluoro-6,6-dimethyl-5a$\alpha$H,13H-(1)benzopyrano(3,2-b)xanthen-13-one;

6,6a$\alpha$-dihydro-6-cyclohexanespiro-5a$\alpha$H,13H-(1)benzopyrano(3,2-b)xanthen-13-one;

6,6a$\alpha$-dihydro-4,8-dimethyl-6-cyclopentanespiro-5a$\alpha$H,13H-(1)benzopyrano(3,2-b)xanthen-13-one;

6,6a$\alpha$-dihydro-3,9-diethyl-6-cycloheptanespiro-5a$\alpha$H,13H-(1)benzopyrano(3,2-b)xanthen-13-one;

6,6a$\alpha$-dihydro-3,9-dimethoxy-6-cyclohexanespiro-5a$\alpha$H,13H-(1)benzopyrano(3,2-b)xanthen-13-one;

6,6a$\alpha$-dihydro-4,8-diethoxy-6-cyclopentanespiro-5a$\alpha$H,13H-(1)benzopyrano(3,2-b)xanthen-13-one;

6,6a$\alpha$-dihydro-4,8-dihydroxy-6-cyclohexanespiro-5a$\alpha$H,13H-(1)benzopyrano(3,2-b)xanthen-13-one;

6,6a$\alpha$-dihydro-2,10-dibromo-6,6-dimethyl-5a$\alpha$H,13H-(1)benzopyrano(3,2-b)xanthen-13-one; and the like.

Examples of hexahydrobenzopyranoxanthenones produced by the process of this invention are 6,6a$\alpha$,12,12a$\alpha$,13a$\alpha$,14-hexahydro-6,6-dimethyl-5a$\alpha$H,13H-(1)benzopyrano(3,2-b)xanthen-13-one;

6,6a$\alpha$,12,12a$\alpha$,13a$\alpha$,14-hexahydro-6$\beta$-methyl-6$\alpha$-ethyl-5a$\alpha$H,13H-(1)benzopyrano(3,2-b)xanthen-13-one;

6,6aα,12,12aα,13aα,14-hexahydro-6β-methyl-6α-n-propyl-5aαH,13H-(1)benzopyrano(3,2-b)xanthen-13-one;

6,6aα,12,12aα,13aα,14-hexahydro-6β-methyl-6α-isopropyl-5aαH,13H-(1)benzopyrano(3,2-b)xanthen-13-one;

6,6aα,12,12aα,13aα,14-hexahydro-4,8-dimethyl-6,6-dimethyl-5aαH,13H-(1)benzopyrano(3,2-b)xanthen-13-one;

6,6aα,12,12aα,13aα,14-hexahydro-3,9-diethyl-6,6-dimethyl-5aαH,13H-(1)benzopyrano(3,2-b)xanthen-13-one;

6,6aα,12,12aα,13aα,14-hexahydro-2,10-di-n-propyl-6,6-dimethyl-5aαH,13H-(1)benzopyrano(3,2-b)xanthen-13-one;

6,6aα,12,12aα,13aα,14-hexahydro-2,10-di-t-butyl-6β-methyl-6α-ethyl-5aαH,13H-(1)benzopyrano(3,2-b)xanthen-13-one;

6,6aα,12,12aα,13aα,14-hexahydro-3,9-dimethoxy-6,6-dimethyl-5aαH,13H-(1)benzopyrano(3,2-b)xanthen-13-one;

6,6aα,12,12aα,13aα,14-hexahydro-4,8-diethoxy-6β-methyl-6α-ethyl-5aαH,13H-(1)benzopyrano(3,2-b)xanthen-13-one;

6,6aα,12,12aα,13aα,14-hexahydro-4,8-diisopropoxy-6,6-dimethyl-5aαH,13H-(1)benzopyrano(3,2-b)xanthen-13-one;

6,6aα,12,12aα,13aα,14-hexahydro-3,9-di-n-butoxy-6β-methyl-6α-ispropyl-5aαH,13H-(1)benzopyrano(3,2-b)xanthen-13-one;

6,6aα,12,12aα,13aα,14-hexahydro-4,8-dihydroxy-6,6-dimethyl-5aαH,13H-(1)benzopyrano(3,2-b)xanthen-13-one;

6,6aα,12,12aα,13aα,14-hexahydro-3,9-dicyano-6β-methyl-6α-ethyl-5aαH,13H-(1)benzopyrano(3,2-b)xanthen-13-one;

6,6aα,12,12aα,13aα,14-hexahydro-4,8-dichloro-6β-methyl-6α-isopropyl-5aαH,13H-(1)benzopyrano(3,2-b)xanthen-13-one;

6,6aα,12,12aα,13aα,14-hexahydro-4,8-difluoro-6,6-dimethyl-5aαH,13H-(1)benzopyrano(3,2-b)xanthen-13-one;

6,6aα,12,12aα,13aα,14-hexahydro-2,10-dibromo-6,6-dimethyl-5aαH,13H-(1)benzopyrano(3,2-b)xanthen-13-one;

6,6aα,12,12aβ,13aβ,14-hexahydro-6,6-dimethyl-5aαH,13H-(1)benzopyrano(3,2-b)xanthen-13-one;

6,6aα,12,12aβ,13aβ,14-hexahydro-6β-methyl-6α-ethyl-5aαH,13H-(1)benzopyrano(3,2-b)xanthen-13-one;

6,6aα,12,12aβ,13aβ,14-hexahydro-6β-methyl-6α-n-propyl-5aαH,13H-(1)benzopyrano(3,2-b)xanthen-13-one;

6,6aα,12,12aβ,13aβ,14-hexahydro-4,8-diethyl-6,6-dimethyl-5aαH,13H-(1)benzopyrano(3,2-b)xanthen-13-one;

6,6aα,12,12aβ,13aβ,14-hexahydro-4,8-dimethyl-6,6-dimethyl-5aαH,13H-(1)benzopyrano(3,2-b)xanthen-13-one;

6,6aα,12,12aβ,13aβ,14-hexahydro-3,9-diethyl-6,6-dimethyl-5aαH,13H-(1)benzopyrano(3,2-b)xanthen-13-one;

6,6aα,12,12aβ,13aβ,14-hexahydro-2,10-di-n-propyl-6,6-dimethyl-5aαH,13H-(1)benzopyrano (3,2-b)xanthen-13-one;

6,6aα,12,12aβ,13aβ,14-hexahydro-2,10-di-t-butyl-6β-methyl-6α-ethyl-5aαH,13H-(1)benzopyrano(3,2-b)xanthen-13-one;

6,6aα,12,12aβ,13aβ,14-hexahydro-3,9-dimethoxy-6,6-dimethyl-5aαH,13H-(1H)benzopyrano(3,2-b)xanthen-13-one;

6,6aα,12,12aβ,13aβ,14-hexahydro-4,8-diethoxy-6β-methyl-6α-ethyl-5aαH,13H-(1)benzopyrano(3,2-b)xanthen-13-one;

6,6aα,12,12aβ,13aβ,14-hexahydro-4,8-diisopropoxy-6,6-dimethyl-5aαH,13H-(1)benzopyrano(3,2-b)xanthen-13-one;

6,6aα,12,12aβ,13aβ,14-hexahydro-3,9-di-n-butoxy-6β-methyl-6α-isopropyl-5aαH,13H-(1)benzopyrano(3,2-b)xanthen-13-one;

6,6aα,12,12aβ,13aβ,14-hexahydro-4,8-dihydroxy-6,6-dimethyl-5aαH,13H-(1)benzopyrano(3,2-b)xanthen-13-one;

6,6aα,12,12aβ,13aβ,14-hexahydro-3,9-dicyano-6β-methyl-6α-ethyl-5aαH,13H-(1)benzopyrano(3,2-b)xanthen-13-one;

6,6aα,12,12aα,13aα,14-hexahydro-6-cyclohexanespiro-5aαH,13H-(1)benzopyrano(3,2-b)xanthen-13-one;

6,6aα,12,12aα,13aα,14-hexahydro-6-cyclopentanespiro-5aαH,13H-(1)benzopyrano(3,2-b)xanthen-13-one;

6,6aα,12,12aα,13aα,14-hexahydro-4,8-dimethyl-6-cyclohexanespiro-5aαH,13H-(1)benzopyrano(3,2-b)xanthen-13-one;

6,6aα,12,12aα,13aα,14-hexahydro-3,9-dimethoxy-6-cyclohexanespiro-5aαH,13H-(1)benzopyrano(3,2-b)xanthen-13-one;

6,6aα,12,12aα,13aα,14-hexahydro-4,9-diethoxy-6-cycloheptanespiro-5aαH,13H-(1)benzopyrano(3,2-b)xanthen-13-one;

6,6aα,12,12aα,13aα,14-hexahydro-4,8-dihydroxy-6-cyclohexaspiro-5aαH,13H-(1)benzopyrano(3,2-b)xanthen-13-one;

6,6aα,12,12aα,13aα,14-hexahydro-4,8-dichloro-6-cyclopentanespiro-5aαH,13H-(1)benzopyrano(3,2-b)-xanthen-13-one;

6,6aα,12,12aα,13aα,14-hexahydro-2,10-dibromo-6-cycloheptanespiro-5aαH,13H-(1)benzopyrano(3,2-b)xanthen-13-one;

6,6aα,12,12aβ,13aβ,14-hexahydro-6-cyclopentanehexanespiro-5aαH,13H-(1)benzopyrano(3,2-b)xanthen-13-one;

6,6aα,12,12aβ,13aβ,14-hexahydro-6-cyclohexanespiro-5aαH,13H-(1)benzopyrano(3,2-b)xanthen-13-one;

6,6aα,12,12aβ,13aβ,14-hexahydro-4,8-dimethyl-6-cyclohexanespiro-5aαH,13H-(1)benzopyrano(3,2-b)xanthen-13-one;

6,6aα,12,12aβ,13aβ,14-hexahydro-3,9-diethyl-6-cycloheptanespiro-5aαH,13H-(1)benzopyrano(3,2-b)xanthen-13-one;

6,6aα,12,12aβ,13aβ,14-hexahydro-3,9-dimethoxy-6-cyclopentanespiro-5aαH,13H-(1H)benzopyrano(3,2-b)xanthen-13-one;

6,6aα,12,12aβ,13aβ,14-hexahydro-4,8-diethoxy-6-dyclohexanespiro-5aαH,13H-(1)benzopyrano(3,2-b)xanthen-13-one;

6,6aα,12,12aβ,13aβ,14-hexahydro-4,8-dihydroxy-6-cycloheptanespiro-5aαH,13H-(1)benzopyrano(3,2-b)xanthen-13-one;

6,6aα,12,12aβ,13aβ,14-hexahydro-3,9-dicyano-6-cyclopentanespiro-5aαH,13H-(1)benzopyrano(3,2-b)xanthen-13-one;

6,6aα,12,12aβ,13aβ,14-hexahydro-3,9-diethyl-6-cycloheptanespiro-5aαH,13H-(1)benzopyrano(3,2-b)xanthen-13-one;

6,6aα,12,12aβ,13aβ,14-hexahydro-3,9-dimethoxy-6-cyclopentanespiro-5aαH,13H-(1H)benzopyrano(3,2-b)xanthen-13-one;

6,6aα,12,12aβ,13aβ,14-hexahydro-4,8-diethoxy-6-cyclohexanespiro-5aαH,13H-(1)benzopyrano(3,2-b)xanthen-13-one;

6,6aα,12,12aβ,13aβ,14-hexahydro-4,8-dihydroxy-6-cycloheptanespiro-5aαH,13H-(1)benzopyrano(3,2-b)xanthen-13-one;

6,6aα,12,12aβ,13aβ,14-hexahydro-3,9-dicyano-6-cyclopentanespiro-5aαH,13H-(1)benzopyrano(3,2-b)xanthen-13-one;

6,6aα,12,12aβ,13aβ,14-hexahydro-4,8-dichloro-6-cyclohexanespiro-5aαH,13H-(1)-benzopyrano(3,2-b)xanthen-13-one;

6,6aα,12,12aβ,13aβ,14-hexahydro-4,8-dichloro-6β-methyl-6α-isopropyl-5aαH,13H-(1)benzopyrano(3,2-b)xanthen-13-one;

6,6aα,12,12aβ,13aβ,14-hexahydro-4,8-difluoro-6,6-dimethyl-5aαH,13H-(1)benzopyrano(3,2-b)xanthen-13-one.

6,6aα,12,12aβ,13aβ,14-hexahydro-2,10-dibromo-6,6-dimethyl-5aαH,13H-(1)benzopyrano(3,2-b)xanthen-13-one; and the like.

The following examples are provided for the purpose of illustrating the process of this invention. They are not intended to be limiting upon the scope of the invention.

EXAMPLE 1

To 75 ml. of acetonitrile containing 5 percent water were added 15.0 grams of tributylamine p-toluene-sulfonate and 4.0 grams of benzoic acid. To the resulting mixture were added 1.0 grams of 6,6aα-dihydro-4,8-dimethoxy-6,6-dimethyl-5aαH,13H-(1)benzopyrano(3,2-b)xanthen-13-one. The solubility of the substrate at 25° C. is about 4–5 mg./ml.; therefore, the substrate remained in the mixture as a suspension. The mixture was placed in the cathode compartment of an electrolytic cell comprising a mercury-pool cathode and a platinum anode. A $-1.6$ volt potential vs. a saturated calomel reference electrode was applied to the cell, and electrolysis was continued until analysis by thin-layer chromatography indicated that the reaction was complete. The reaction mixture was removed from the electrolysis cell, and the solvent was removed. The residue was dissolved in ethyl acetate, and the resulting solution was washed sequentially three times with 1N hydrochloric acid, 3 times with saturated aqueous sodium bicarbonate, 3 times with 1N hydrochloric acid, twice with saturated aqueous sodium bicarbonate, and once with water. Analysis of the product by high-pressure liquid chromatography (HPLC) indicated that approximately 65% of 6,6aα,12,12aα,13aα,14-hexahydro-4,8-dimethoxy-6,6-dimethyl-5aαH,13H-(1)benzopyrano(3,2-b)xanthen-13-one was formed. The ethyl acetate was removed, and the product was dried. The product was crystallized from a mixture of methanol and chloroform to obtain approximately a 50% yield of the above compound in approximately 90% purity.

EXAMPLE 2

Employing the procedure of Example 1, a mixture of 0.8 gram of lithium perchlorate and 4.0 ml. of glacial acetic acid in 75 ml. of acetonitrile containing 5% water was prepared. To the resulting mixture was added 1 gram of 6,6aα-dihydro-4,8-dimethoxy-6,6-dimethyl-5aαH,13H-(1)benzopyrano-(3,2-b)xanthen-13-one. The resulting mixture was subjected to electrolytic reduction at a mercury-pool cathode and platinum anode at 25° C. and at constant $-1.5$ volt potential. vs. a saturated calomel reference electrode. Upon workup and crystallization from chloroform-methanol, 6,6aα,1-2aβ,13aβ,14-hexahydro-4,8-dimethoxy-6,6-dimethyl-5aαH,13H-(1)benzopyrano(3,2-b)xanthen-13-one was obtained as white to cream-colored platelets in approximately 65% yield. The product had a purity of approximately 92%. Melting point 235°–245° C. (est).

EXAMPLE 3

Employing the procedure of Example 1, to a mixture of 50 ml. of N,N-dimethylformamide containing 5% water were added 2 g. of benzoic acid and an amount of tetrabutylammonium perchlorate sufficient to achieve a 0.2 M concentration. To the resulting mixture then were added 100 mg. of 6,6aα-dihydro-4,8-dimethoxy-6,6-dimethyl-5aαH,13H-(1)benzopyrano(3,2-b)xanthen-13-one. The resulting mixture was subjected to electrolytic reduction at a mercury-pool cathode at 25° C. and at constant $-1.6$ volt potential vs. a saturated calomel reference electrode. Upon workup and crystallization, 6,6aα,12aα,13aα,14-hexahydro-4,8-dimethoxy-6,6-dimethyl-5aαH,13H-(1)benzopyrano(3,2-b)xanthen-13-one was obtained in approximately 70% yield.

EXAMPLE 4

Employing the procedure of Example 1, to a mixture of 60 ml. of methanol and 4.8 ml. of glacial acetic acid were added an amount of tetrabutylammonium chloride sufficient to achieve a 0.1 M concentration. To the resulting mixture then were added 100 mg. of 6,6aα-dihydro-4,8-dimethoxy-6,6-dimethyl-5aαH,13H-(1)benzopyrano(3,2-b)xanthen-13-one. The resulting mixture was subjected to electrolytic reduction at a mercury-pool cathode at 25° C. and at constant $-1.4$ volt potential vs. a saturated calomel reference electrode. Upon workup and crystallization, 6,6aα,12aα,13aα,14-hexahydro-4,8-dimethoxy-6,6-dimethyl-5aα, H,13H-(1)benzopyrano(3,2-b)xanthen-13-one was obtained in approximately 85% yield.

EXAMPLE 5

Employing the procedure of Example 1, a mixture of 2.57 grams of tetrabutylammonium perchlorate and 2.5 grams of benzoic acid in 50 ml. of toluene and 25 ml. of methanol was prepared. To the resulting mixture then were added 300 mg. of 6,6aα-dihydro-4,8-dimethoxy-6,6-dimethyl-5aαH,13H-(1)benzopyrano(3,2-b)xanthen-13-one. The resulting mixture was subjected to electrolytic reduction at a mercury-pool cathode at 25° C. and at constant $-1.6$ volt potential vs. a saturated calomel reference electrode. Upon workup and crystallization, 6,6aα,12aα,13aα,14-hexahydro-4,8-dimethoxy-6,6-dimethyl-5aαH,13H-(1)benzopyrano(3,2-b)xanthen-13-one was obtained in approximately 65% yield.

EXAMPLE 6

Employing the procedure of Example 1, to a mixture of 75 ml. of acetonitrile containing 5% acetic acid and 5% water were added an amount of tetra-n-hexylammonium chloride sufficient to achieve a 0.1 M concentration. To the resulting mixture then were added 200 mg. of 6,6aα-dihydro-4,8-dimethoxy-6,6-dimethyl-5aαH,13H-(1)benzopyrano-(3,2-b)xanthen-13-one. The resulting mixture was subjected to electrolytic reduction at a mercury-pool cathode at 25° C. and at constant 1.7 volt potential vs. a saturated calomel reference electrode. High pressure liquid chromatography (HPLC) indicated the presence of 6,6aα,12aα,13aα,14-hexahydro-4,8-dimethoxy-6,6-dimethyl-5aαH,13H-(1)benzopyrano(3,2-b)xanthen-13-one in approximately 65% yield.

EXAMPLE 7

Employing the procedure of Example 1, to a mixture of 75 ml. of acetonitrile containing 5% acetic acid were added an amount of methyltrictylammonium chloride (aliquot 336) sufficient to achieve a 0.1 M concentration. To the resulting mixture then were added 200 mg. of 6,6aα-dihydro-4,8-dimethoxy-6,6-dimethyl-5aαH,13H-(1)benzopyrano(3,2-b)-xanthen-13-one. The resulting mixture was subjected to electrolytic reduction at a mercury-pool cathode at 25° C. and at constant 1.6 volt potential vs. a saturated calomel reference electrode. HPLC indicated the presence of 6,6aα,12aα,13aα,14-hexahydro-4,8-dimethoxy-6,6-dimethyl-5aα,H,13H-(1)benzopyrano(3,2-b)xanthen-13-one in approximately 65–70% yield.

EXAMPLE 8

Employing the procedure of Example 1, to a mixture of 67 ml. of acetonitrile containing 5% water and 1.5% acetic acid were added an amount of N,N-diisopropylethylamine tosylate sufficient to achieve a 0.1 M concentration. To the resulting mixture then were added 100 mg. of 6,6aα-dihydro-4,8-dimethoxy-6,6-dimethyl-5aαH,13H-(1)benzopyrano-(3,2-b)xanthen-13-one. The resulting mixture was subjected to electrolytic reduction at a mercury-pool cathode at 25° C. and at constant −1.5 volt potential vs. a saturated calomel reference electrode. HPLC indicated the presence of 6,6aα,1-2aα,13aα,14-hexahydro-4,8-dimethoxy-6,6-dimethyl-5aα,H,13H-(1)benzopyrano(3,2-b)xanthen-13-one in approximately 60°–65° C yield.

We claim:

1. A process for preparing a compound of the formula

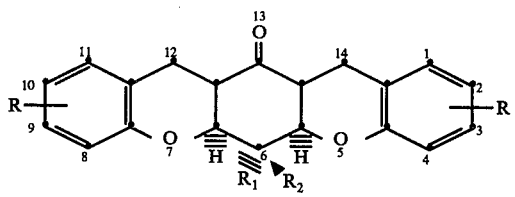

which comprises electrolytically reducing a compound of the formula

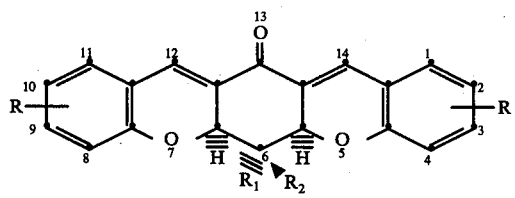

in which, in any of the above, each R is hydrogen, $C_1$–$C_4$ alkyl, $C_1$–$C_4$ alkoxy, hydroxy, cyano, or halo, and both R groups are identical and are symmetrically located; $R_1$ is $C_1$–$C_3$ alkyl and $R_2$ is methyl, or $R_1$ and $R_2$ taken together are $+CH_2)_n$ in which $n$ is an integer from 4 to 6; such electrolytic reduction being carried out at a temperature of from about 5° C. to about 80° C. in an organic or an aqueous-organic medium at a mercury cathode in the presence of a proton source having pKa values of from about 2 to about 6 and in the presence of an electrolyte selected from the group consisting of alkali metal salts, quaternary ammonium salts having a total of about 10 to about 28 carbon atoms in the cation moiety, and tertiary amine salts having a total of about 7 to about 21 carbon atoms in the cation moiety.

2. Process of claim 1, in which the reduction is carried out at a temperature of from about 20° C. to about 30° C.

3. Process of claim 2, in which the reduction is carried out using, as electrolyte, an alkali metal salt.

4. Process of claim 2, in which the reduction is carried out in the presence of an electrolyte selected from the group consisting of quaternary ammonium salts having a total of about 10 to about 28 carbon atoms in the cation moiety and tertiary amine salts having a total of about 7 to about 21 carbon atoms in the cation moiety.

5. Process of claim 4, in which the reduction is carried out using, as electrolyte, a quaternary ammonium salt having a total of about 10 to about 28 carbon atoms in the cation moiety.

6. Process of claim 5, in which the electrolyte is a tetrabutylammonium salt.

7. Process of claim 4, in which the reduction is carried out using, as electrolyte, a tertiary amine salt having a total of about 7 to about 21 carbon atoms in the cation moiety.

8. Process of claim 7, in which the electrolyte is a tributylamine salt.

9. Process of claim 1, in which the reduction is carried out on a compound in which $R_1$ is $C_1$–$C_3$ alkyl.

10. Process of claim 9, in which $R_1$ is methyl.

11. Process of claim 10, in which each R is $C_1$–$C_4$ alkoxy.

12. Process of claim 11, in which each R is methoxy.

13. Process of claim 12, in which the R groups are located in the 4- and 8-positions.

14. Process of claim 10, in which each R is hydrogen.

* * * * *